(12) United States Patent
Fix

(10) Patent No.: US 8,979,828 B2
(45) Date of Patent: Mar. 17, 2015

(54) TAPERED LIQUID LIGHT GUIDE

(75) Inventor: Clint Fix, Grand Junction, CO (US)

(73) Assignee: The Spectranetics Corporation, Colorado Springs, CO (US)

( * ) Notice: Subject to any disclaimer, the term of this patent is extended or adjusted under 35 U.S.C. 154(b) by 1603 days.

(21) Appl. No.: 12/176,886

(22) Filed: Jul. 21, 2008

(65) Prior Publication Data

US 2010/0016842 A1    Jan. 21, 2010

(51) Int. Cl.
*A61B 18/24* (2006.01)
*A61B 18/20* (2006.01)

(52) U.S. Cl.
CPC ......... *A61B 18/245* (2013.01); *A61B 2018/206* (2013.01)
USPC .......................................................... 606/2

(58) Field of Classification Search
None
See application file for complete search history.

(56) References Cited

U.S. PATENT DOCUMENTS

| | | | |
|---|---|---|---|
| 4,053,845 A | 10/1977 | Gould | |
| 4,564,011 A * | 1/1986 | Goldman | ........................ 606/9 |
| 4,641,912 A | 2/1987 | Goldenberg | |
| 4,686,979 A | 8/1987 | Gruen | |
| 4,732,448 A | 3/1988 | Goldenberg | |
| 4,747,405 A | 5/1988 | Leckrone | |
| 4,784,132 A | 11/1988 | Fox et al. | |
| 4,799,754 A | 1/1989 | Goldenberg | |
| 4,807,620 A | 2/1989 | Sturl | |
| 4,830,460 A | 5/1989 | Goldenberg | |
| 4,844,062 A | 7/1989 | Wells | |
| 4,848,336 A | 7/1989 | Fox et al. | |
| 4,924,863 A | 5/1990 | Sterzer | |
| 5,016,964 A | 5/1991 | Donnelly | |
| 5,041,108 A | 8/1991 | Fox et al. | |
| 5,112,328 A | 5/1992 | Taboada et al. | |
| 5,188,632 A | 2/1993 | Goldenberg | |
| 5,246,437 A * | 9/1993 | Abela | ........................... 606/15 |
| 5,250,045 A | 10/1993 | Bohley | |
| 5,263,952 A | 11/1993 | Grace | |
| 5,267,341 A | 11/1993 | Shearin | |
| 5,304,171 A | 4/1994 | Gregory | |
| 5,350,375 A | 9/1994 | Deckelbaum et al. | |
| 5,352,197 A | 10/1994 | Hammersmark | |
| 5,415,653 A | 5/1995 | Wardle | |
| 5,429,604 A | 7/1995 | Solar | |
| 5,429,617 A | 7/1995 | Hammersmark | |

(Continued)

OTHER PUBLICATIONS

Gregory et al. (IEEE Journal of Quantum Electronics 1990, 26(12):2289-2296).*

(Continued)

*Primary Examiner* — Ernst V Arnold
(74) *Attorney, Agent, or Firm* — Faegre Baker Daniels LLP

(57) ABSTRACT

A catheter tip is provided according to various embodiments of the disclosure. The catheter tip may comprise a distal end, a proximal end, and tubular walls. The distal end includes a distal aperture with a distal inside diameter, and the proximal end includes a proximal aperture with a proximal inside diameter. The proximal inside diameter may be greater than the distal inside diameter. The proximal end comprises attachment means configured to couple the proximal end with a distal end of a laser catheter. The tubular walls may include at least an inside taper from the proximal end to the distal end such that the inner tubular walls generally taper from the proximal inside diameter to the distal inside diameter. Moreover, the tubular walls may be configured to direct at least a liquid medium, for example, a biocompatible solution, toward the distal aperture.

21 Claims, 6 Drawing Sheets

(56) References Cited

U.S. PATENT DOCUMENTS

| | | | |
|---|---|---|---|
| 5,440,664 A | 8/1995 | Harrington et al. | |
| 5,456,680 A | 10/1995 | Taylor et al. | |
| 5,470,330 A * | 11/1995 | Goldenberg et al. | 606/7 |
| 5,484,433 A | 1/1996 | Taylor et al. | |
| 5,514,128 A | 5/1996 | Kasprzyk et al. | |
| 5,571,151 A | 11/1996 | Gregory | |
| 5,573,531 A | 11/1996 | Gregory | |
| 5,607,419 A | 3/1997 | Amplatz et al. | |
| 5,623,940 A | 4/1997 | Daikuzono | |
| 5,643,251 A | 7/1997 | Kasprzyk et al. | |
| 5,649,923 A | 7/1997 | Gregory | |
| 5,722,972 A | 3/1998 | Power et al. | |
| 5,817,144 A | 10/1998 | Gregory | |
| 5,824,026 A | 10/1998 | Diaz | |
| 5,836,946 A | 11/1998 | Diaz | |
| RE36,104 E | 2/1999 | Solar | |
| 5,976,124 A | 11/1999 | Reiser | |
| 5,989,243 A | 11/1999 | Goldenberg | |
| 6,022,342 A | 2/2000 | Mukherjee | |
| 6,039,726 A | 3/2000 | Lewis et al. | |
| 6,066,130 A | 5/2000 | Gregory | |
| 6,117,128 A * | 9/2000 | Gregory | 606/7 |
| 6,156,029 A | 12/2000 | Mueller | |
| 6,163,641 A | 12/2000 | Eastgate | |
| 6,290,668 B1 | 9/2001 | Gregory | |
| 6,458,098 B1 | 10/2002 | Kanesaka | |
| 6,743,208 B1 | 6/2004 | Coyle | |
| 6,963,688 B2 | 11/2005 | Nath | |
| 2003/0216685 A1 | 11/2003 | Porter | |
| 2006/0013533 A1 | 1/2006 | Slatkine | |
| 2009/0254074 A1 | 10/2009 | Splinter et al. | |

OTHER PUBLICATIONS

Walker et al. (British Journal of Pharmacology 2000, 130:242-248).*
U.S. Appl. No. 12/061,430, filed Apr. 2, 2008, Splinter et al.
Grundfest et al. "Laser Ablation of Human Atherosclerotic Plaque Without Adjacent Tissue Injury," JACC, Apr. 1985, vol. 5, No. 4, pp. 929-933.
Official Action for U.S. Appl. No. 12/061,430, mailed Dec. 19, 2008, 10 pages.
Official Action for U.S. Appl. No. 12/254,254, mailed Jul. 2, 2012, 14 pages.

* cited by examiner

TAPERED LIQUID LIGHT GUIDE

BACKGROUND

This disclosure relates in general to liquid light guides and, but not by way of limitation, to liquid light guides used in conjunction with a laser catheter among other things.

Catheters containing optical fibers transmit energy to irradiate internal parts of the body for diagnostic and therapeutic purposes. There are many medical applications in which it is desirable to deliver energy, such as laser energy, through an optical fiber or similar waveguide device disposed in a body cavity for treatment or diagnosis. These include, among others, the ablation of tissue such as plaque, calcium, and tumors, the destruction of calculi, and the heating of bleeding vessels for coagulation. Some ablation targets, such as, calcified endovascular lesions, for example, can be especially difficult to ablate. The lasers used may produce either pulsed or continuous-wave light of wavelengths ranging from the ultraviolet to the infra-red.

BRIEF SUMMARY

A catheter tip is provided according to one embodiment. The catheter tip may comprise a distal end, a proximal end, and tubular walls. The distal end includes a distal aperture with a distal inside diameter, and the proximal end includes a proximal aperture with a proximal inside diameter. The proximal inside diameter may be greater than the distal inside diameter. The proximal end comprises attachment means configured to couple the proximal end with a distal end of a laser catheter. The tubular walls may include at least an inside taper from the proximal end to the distal end such that the inner tubular walls generally taper from the proximal inside diameter to the distal inside diameter. Moreover, the tubular walls may be configured to direct at least a liquid medium, for example, a biocompatible solution, toward the distal aperture. In some embodiments, the tubular walls comprise a material with an index of refractive approximately less than or equal to the index of refraction of the liquid medium.

A tapered support sheath is also provided according to another embodiment. The tapered support sheath may include a proximal end including a proximal aperture configured to receive a laser catheter, a distal end including a distal aperture, and an elongated tubular structure. In some embodiments, the inside diameter of the distal aperture is less than the inside diameter of the proximal aperture. The elongated tubular structure may include an inner lumen that extends from the proximal end to the distal end and may include a taper. The elongated tubular structure may also be configured to support a laser catheter within at least a portion of the inner lumen such that the laser catheter directs light toward the distal aperture. In other embodiments, the elongated tubular structure may be configured to allow a liquid medium to flow toward the distal end within the inner lumen. The tapered support sheath may also include a liquid medium infusion port at or near the proximal end of the sheath.

A device for increasing the energy density of light emanating from a laser catheter is also disclosed according to one embodiment. The device may include a proximal end, a distal end, an elongated tubular structure, coupling means, directing means and concentrating means. The elongated tubular structure may include an inner lumen and extend from the proximal end to the distal end. The elongated tubular structure may be configured to allow a liquid medium to flow through the inner lumen toward the distal end. The coupling means may include means for coupling the device with the laser catheter. The directing means may include means for directing light through at least a portion of the device toward a target. The concentrating means may include means for increasing the energy density of the light beam exiting the device compared with the energy density of the light beam entering said device.

A tapered liquid light guide is disclosed according to another embodiment that includes a distal end with a distal aperture, a proximal end with a proximal aperture, and a body. The cross-section of the proximal aperture is greater than the cross-section of the distal aperture. The body may include an inner lumen; a portion of which is tapered. At least a portion of the inner lumen includes a material with an index-of-refraction which is lower than the inner liquid medium. The inner lumen is also configured to allow a liquid medium to flow toward the distal end.

A tapered liquid light guide is disclosed according to another embodiment that includes a distal end with a distal aperture, a proximal end with a proximal aperture, and a body. The cross-section of the distal aperture is greater than the cross-section of the proximal aperture. The body may include an inner lumen; a portion of which is tapered. At least a portion of the inner lumen includes a material with an index-of-refraction which is lower than the inner liquid medium. The inner lumen is also configured to allow a liquid medium to flow toward the distal end.

Further areas of applicability of the present disclosure will become apparent from the detailed description provided hereinafter. It should be understood that the detailed description and specific examples, while indicating various embodiments, are intended for purposes of illustration only and do not limit the scope of the disclosure.

Figure 1:
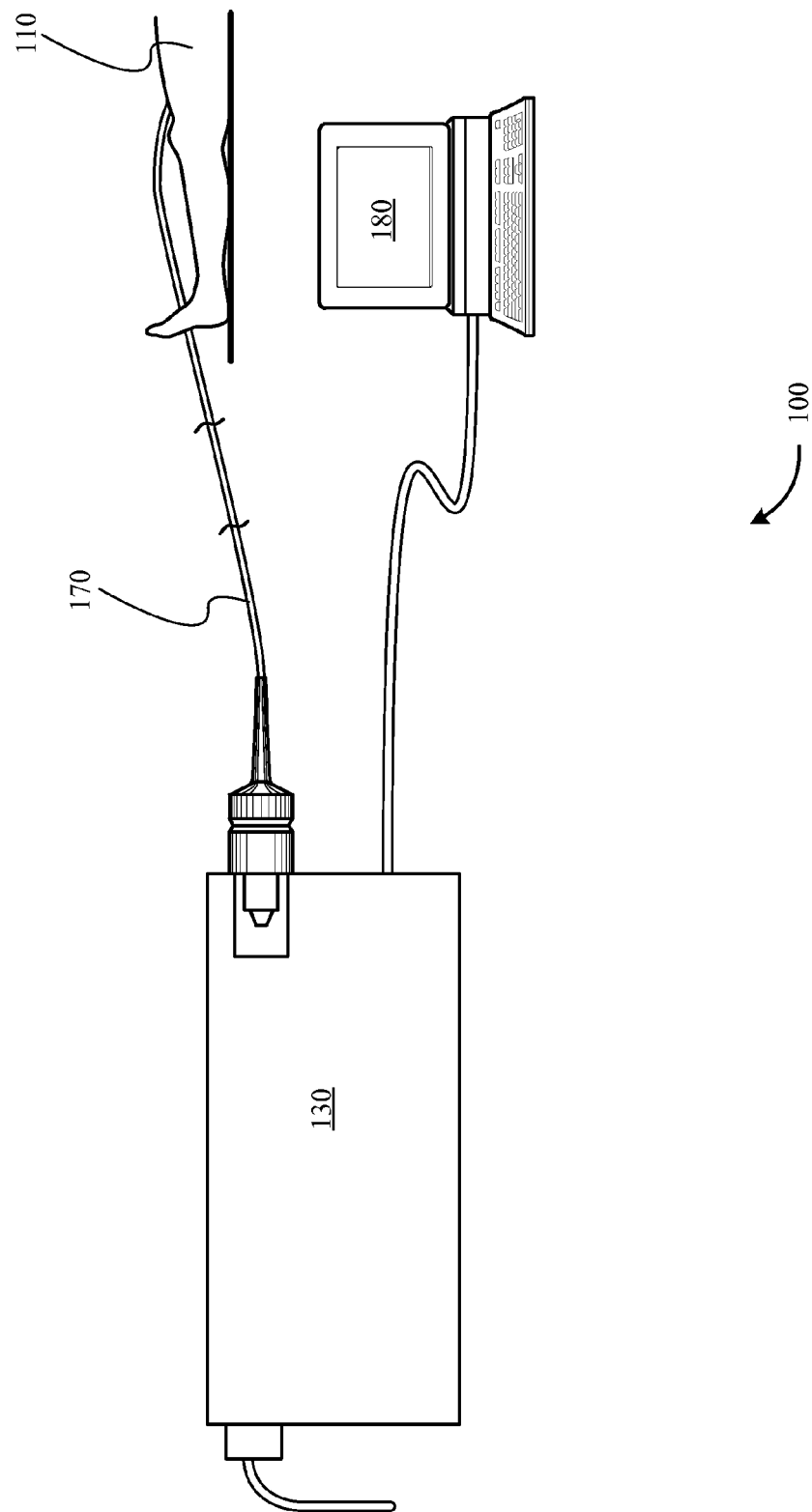
FIG. 1 shows a laser catheter system according to one embodiment.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It should be understood that various changes may be made in the function and arrangement of elements without departing from the spirit and scope as set forth in the appended claims.

Embodiments described throughout this disclosure provide for tips, sheaths, catheters, and/or devices that increase the energy density of a laser catheter. Some embodiments use tapered liquid light guides that decrease the beam cross-section of laser light in order to increase the energy density. Such energy density increases may be useful for ablating stubborn lesions, occlusions, obstructions, etc. Moreover, many of the embodiments are directed to devices that may be accessories to a standard laser catheter. For example, various embodiments include detachable and/or replaceable catheter tips and/or sheaths.

A tapered catheter tip is provided according to one embodiment. Such a tapered catheter tip may be coupled with a laser catheter. The taper provides a decrease in the laser spot size and, therefore, an increase in the energy density of laser light. Such tips, in one embodiment, may be constructed of material with an index of refraction which is lower than the liquid medium on the inner lumen at the tip in order to induce internal reflection from within the liquid core. In another embodiment, a tip may be constructed of a material that provides low light attenuation. In some embodiments the laser catheter may provide light in the ultraviolet range. Moreover, the tapered catheter tip may direct a liquid medium from the proximal end of the tip toward the distal end of the tip.

In use, a user may be performing laser ablation within patient using a liquid light guide laser catheter. In this example, the laser catheter may operate with 308 nm UVB light and the laser catheter may use a range of solutions such as NaCl solution as the liquid light guide medium. At some point in the procedure the doctor may encounter a target that is difficult to ablate with the laser catheter, such as, calcified endovascular lesions. In such a case, an increased laser density may provide better ablation. Accordingly, the doctor may remove the laser catheter, attach a tapered catheter tip. The tapered catheter tip narrows the spot size of the laser light emanating from the laser catheter while transmitting roughly the same laser energy. The doctor may then reinsert the laser catheter and ablate the difficult target using the tapered tip. Following ablation, the doctor may remove the tip or continue ablation with the tapered tip.

Some embodiments provide a tapered catheter sheath. Such a catheter sheath may be an elongated tubular structure that accepts a laser catheter through much of the elongated portion thereof. In other embodiments the elongated tubular structure accepts a laser catheter through all, most of all, or a portion thereof. In some embodiments the catheter sheath is tapered at the distal end to decrease the spot size of the laser light. In other embodiments the catheter sheath may include an infusion port that provides biocompatible fluid delivery through the sheath toward the distal end of the sheath. In another embodiment, a sheath may be constructed of a material that provides low attenuation of light. In some embodiments the sheath or at least a tapered portion of the sheath may be constructed of material with a low index of refraction in order to induce total internal reflection. In some embodiments the laser catheter may provide light in the ultraviolet range.

FIG. 1 shows a laser catheter system 100 according to one embodiment. A laser 130 is shown coupled with a user interface 180. In this embodiment the user interface 180 is computer programmed to control the laser 130. The laser, for example, may be an excimer laser. The laser, for example, may also produce light in the ultraviolet range. The laser is connected with a catheter 170 that may be inserted into a vessel of the human body 110. The laser catheter system 100 may employ one or more tapered waveguides that guide laser light from the laser 130 through the catheter 170 toward a target.

Figure 2:
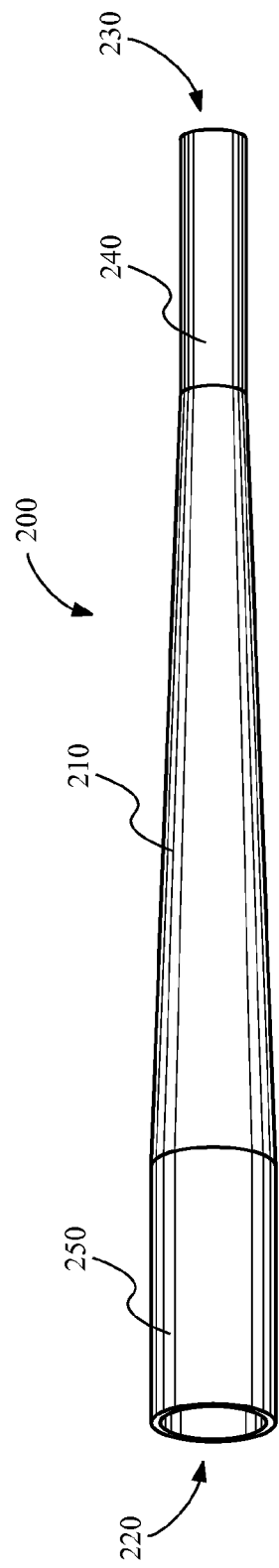
FIG. 2 shows a tapered liquid light guide tip according to one embodiment.

FIG. 2 shows a tapered liquid light guide tip 200 according to one embodiment. The liquid light guide tip 200 includes a distal end 230 and a proximal end 220. In this embodiment both the distal end 230 and the proximal end 220 include apertures. As shown in the figure the tip includes a tapered portion 210 between the proximal end 220 and the distal end 230. In some embodiments, the proximal end 220 of the tapered liquid light guide tip may be coupled with a laser catheter, a liquid light guide 200, or both.

Figure 3:
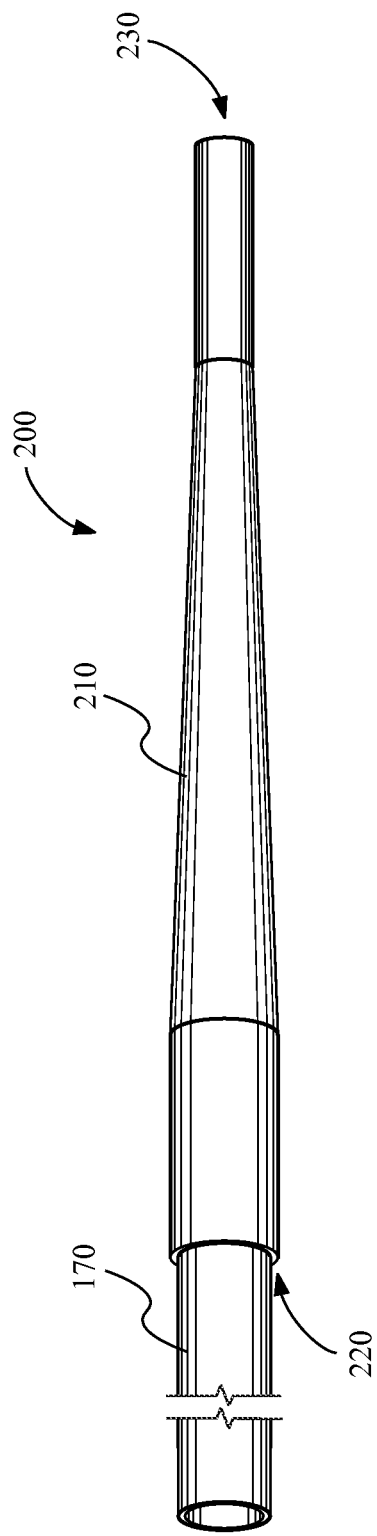
FIG. 3 shows a tapered liquid light guide tip coupled with a laser catheter according to one embodiment.

FIG. 3 shows the proximal end 220 of a tapered liquid light guide tip 200 coupled with a laser catheter 170 according to one embodiment. Only a portion of the laser catheter 170 is shown. When coupled with a laser catheter 170, the liquid light guide tip 200 may direct laser light with a more concentrated spot beam toward a target from the distal end 230. In doing so, the energy density of the light incident on a target from the laser catheter 170 through the liquid light guide tip 200 is increased due to the decrease in spot size. The laser catheter 170 may also provide a biocompatible fluid that flows through the liquid light guide tip 200 from the proximal end 220 toward the distal end 230. In order to decrease the spot size of the laser beam through the tip, total internal reflection must be maintained through the taper 210 of the liquid light guide tip 200. Total internal reflection can be maintained when the biocompatible fluid has a index of refraction greater than the index of refraction of the lining of the tubing.

The biocompatible fluid, in some embodiments, may include a saline solution. In other embodiments the biocompatible fluid may include $MgCl_2$, NaCl, CaCl, etc. In other embodiments the biocompatible fluid may include a solution comprising, for example, Ca, Mg, Mn, Ni, Cl, and/or Co. In some embodiments, the biocompatible fluid may include lactated Ringer's solution. The lactated Ringer's solution, for example, may come from sodium chloride (NaCl), sodium lactate ($NaC_3H_5O_3$), calcium chloride ($CaCl_2$), and/or potassium chloride (KCl). Those of skill in the art will recognize that other combinations of salts may be used. In some embodiments, magnesium chloride and lactated Ringer's solution have good biocompatibility (e.g., low toxicity) as well as good light transmission characteristics at the 308 nm wavelength. The biocompatible fluid may be tailored to the wavelength of light produced by the laser. For example, waveguides including a biocompatible fluid of approximately 15% to approximately 60% w/w $CaCl_2$ transmit light well in the infrared, but only partially in the ultraviolet region. Also, such waveguides generally do not transmit well below 250 nm. There are many types of biocompatible fluids that may be used without limitation. Moreover, embodiments described herein are not limited to specific biocompatible fluid.

The body and/or walls of the tapered liquid light guide tip 200 may comprise any low index material without limitation. For example, a material with an index or refraction below the index of refraction of water, approximately 1.4 at the 308 nm wavelength. These materials may include, for example, Teflon AF2400 tubing made by DuPont. In other embodiments, the walls may include any fluoropolymer, such as, for example, Hyflon® PFA or MFA, FEP, KEL-F, Teflon PFA, Tefzel, Fluon, Tedlar, ECTFE, PVDF, PCTFE, FFKM, Kalrez, Viton, Krytox, and 3M THV-500. Polyethylene, PVC, polycarbonate and/or other plastics may be used in some embodiments.

The tapered liquid light guide tip 200 may include portions without a taper. For example, as shown in FIG. 2 the tip 200 may include a extended portion 250 near the proximal end and/or a extended portion 240 near the distal end. While the extended portion 250 and/or the distal aperture is shown with a circular cross section, any shape may be used. For example, the cross section may be oval or polygon shaped. Moreover, in another embodiment the distal end may taper directly to the distal aperture 230 without a substantially extended portion. In another embodiment, the tip may be substantially cone shaped. In such an embodiment, the tip may have substantially no extended portions.

Figure 4:
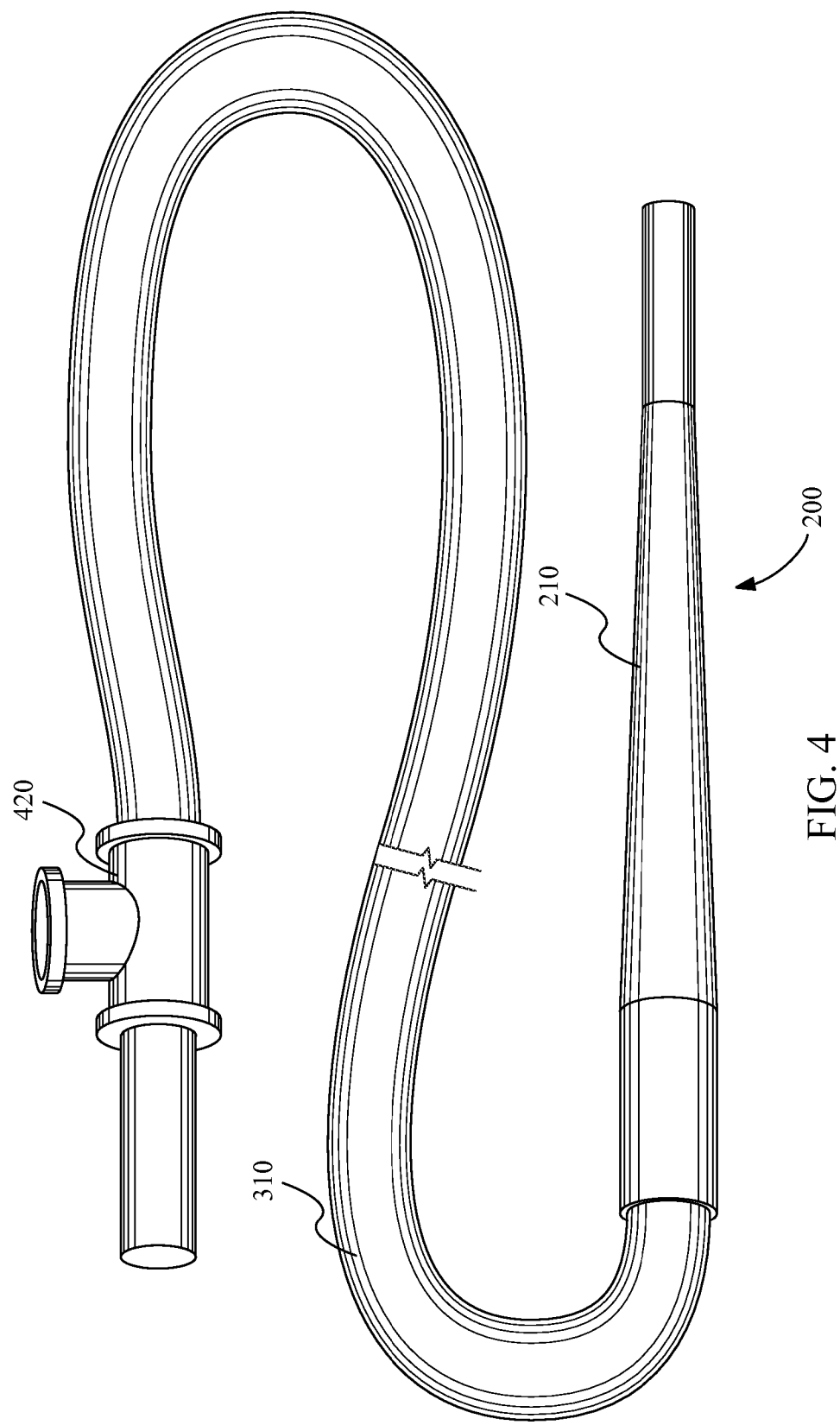
FIG. 4 shows a liquid light guide catheter coupled with a tapered liquid light guide tip according to one embodiment.

FIG. 4 shows a liquid light guide catheter 210 coupled with a tapered liquid light guide tip 200 according to one embodiment. The liquid light guide catheter 210 also includes an infusion port 420 for introducing a biocompatible material into the laser catheter 210. The biocompatible material may act as a light guide within the laser catheter that channels light from the proximal end through toward the distal end. The tapered liquid light guide tip 200 includes a tapered portion 210.

Figure 5A:
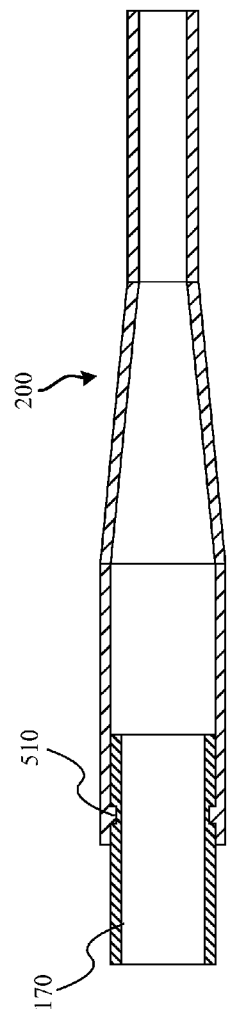
FIGS. 5A-5C show tapered liquid light guide tips with various attachment mechanisms according to various embodiments.
Figure 5B:
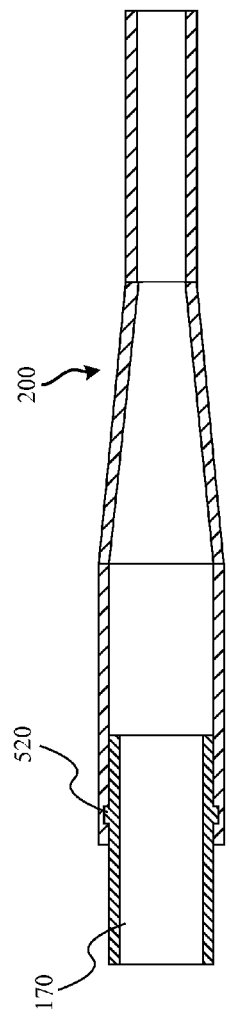
Figure 5C:
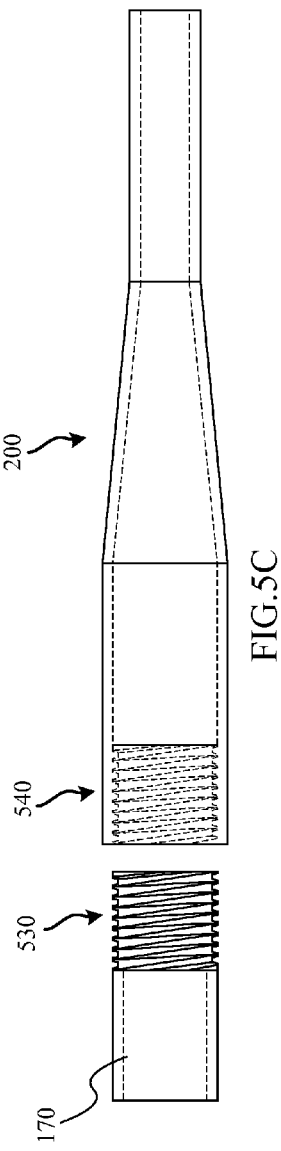

FIGS. 5A-5C show tapered liquid light guide tips with various attachment mechanisms according to various embodiments. FIG. 5A shows an attachment mechanism such that a ring 510 on the inside of the tip catches a grove on the catheter according to one embodiment. In some embodiments, at least a portion or all of the attachment mechanism comprises a shape-memory material that shrinks when heated to about the body temperature. Shrinking may more tightly secure the tip to the laser catheter when used within a body. In FIG. 5B a ring 520 is on the exterior of the laser catheter and the grove is on the interior of the tip 200 according to another embodiment. FIG. 5C shows the tip with threads 540 on the interior and the laser catheter with threads 530 on the exterior. Of course, the threads may be on the exterior of the tip and the interior of the laser catheter according to another embodiment. Various other attachment mechanisms may also be used without deviating from the spirit and scope of this disclosure. For example, clips, detents, rings, washers, pins, bushings, o-rings, etc., may be used as part of the attachment mechanism. In some embodiments, the tapered liquid light guide tip may be attached using an X-Ray contrast medium, a sticky material or any adhesive.

Figure 6:
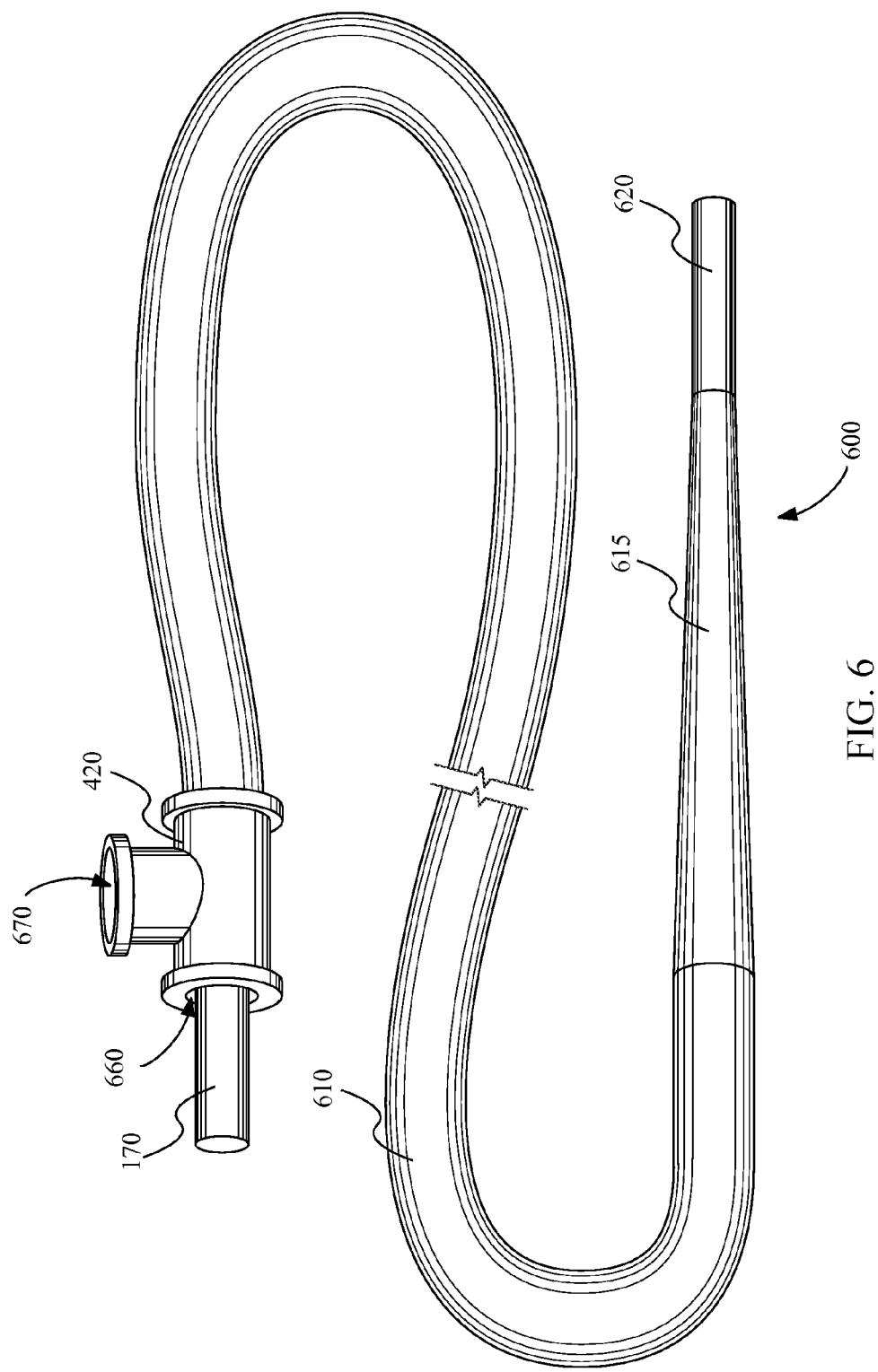
FIG. 6 shows a tapered liquid light guide sheath according to one embodiment.

FIG. 6 shows a tapered liquid light guide sheath 600 according to another embodiment. The liquid light guide sheath 600 may include an elongated tubular body 610, a tapered portion 615, a distal aperture, an inner lumen, and an infusion port 420. The infusion port 640 includes a catheter port 660 that receives a laser catheter 170 or other light channeling device. The catheter port is configured to allow a catheter, such as a laser catheter, to be fed into the inner lumen of the sheath 600. The sheath 600 may also include a fluid port 670 that may be coupled, for example, with a biocompatible fluid delivery device. The fluid port 670 may receive biocompatible fluid that flows through the inner lumen of the sheath 600. The biocompatible fluid may be used as a light guide within portions of the sheath. In some embodiments, the liquid light guide sheath may include a distal extended portion 620, while in other embodiments the sheath tapers substantially directly to the distal aperture.

The tapered liquid light guide sheath 600 may be used to direct laser light from a catheter and biocompatible fluid toward a target. The laser catheter 170 may slide within the inner lumen from the infusion port 420 toward the distal end. Portions of the sheath 600 may act as a liquid light guide directing light from the laser catheter through a distal aperture toward a target. Accordingly, in some embodiments, portions or some portions of the tapered liquid light guide sheath 600 may comprise a low index material and/or a low attenuation material. The type of material chosen as well as the type of biocompatible fluid used within the light guide may be chosen based on the wavelength of light produced by the laser catheter.

Specific details are given in the above description to provide a thorough understanding of the embodiments. However, it is understood that the embodiments may be practiced without these specific details. For example, circuits, structures, and/or components may be shown in block diagrams in order not to obscure the embodiments in unnecessary detail. In other instances, well-known circuits, processes, algorithms, structures, components, and techniques may be shown without unnecessary detail in order to avoid obscuring the embodiments.

While the principles of the disclosure have been described above in connection with specific apparatuses and methods this description is made only by way of example and not as limitation on the scope of the disclosure.

What is claimed is:

1. A tapered liquid light guide configured to increase energy density of light emanating from a laser catheter, the tapered liquid light guide comprising:
   a proximal end including a proximal aperture having an inside diameter;
   coupling means for mechanically and detachably coupling the proximal end to a distal end of the laser catheter;
   a distal end including a distal aperture having an inside diameter, wherein the inside diameter of the distal aperture is less than the inside diameter of the proximal aperture; and
   an elongated tubular structure including an inner lumen and extending from the proximal end to the distal end, wherein the elongated tubular structure is configured to direct light received from the proximal aperture toward the distal aperture, wherein the elongated tubular structure is configured to allow a liquid medium to flow toward the distal end within the inner lumen, wherein at least a portion of the inner lumen includes a taper from a first cross-section adjacent to the proximal end to a second cross-section adjacent to the distal end, wherein the first cross-section is greater than the second cross-section, and wherein at least a portion of the tapered portion of the inner lumen is constructed from a material configured to induce internal reflection of light within the liquid medium.

2. The tapered liquid light guide according to claim 1, further comprising a liquid medium infusion port at or near the proximal end.

3. The tapered liquid light guide according to claim 1, wherein the liquid medium comprises a biocompatible solution.

4. The tapered liquid light guide according to claim 1, wherein the liquid medium comprises a solution comprising a salt selected from the group consisting of $MgCl_2$, NaCl and CaCl.

5. The tapered liquid light guide according to claim 1, wherein the liquid medium comprises a salt solution.

6. The tapered liquid light guide according to claim 1, wherein at least a portion of the inner lumen taper is approximately near the distal end.

7. A tapered liquid light guide for increasing the energy density of light emanating from a laser catheter, the tapered liquid light guide comprising:
   a proximal end;
   a distal end;

an elongated tubular structure including an inner lumen and extending from the proximal end to the distal end, wherein the elongated tubular structure is configured to direct light from the laser catheter through the inner lumen and is configured to allow a liquid medium to flow through the inner lumen toward the distal end, wherein at least a portion of the inner lumen is constructed from a material configured to induce internal reflection of light within the liquid medium;

coupling means for mechanically and detachably coupling the proximal end of the device with a distal end of the laser catheter;

directing means for directing light through at least a portion of the device toward a target; and concentrating means for increasing the energy density of the light beam exiting the device compared with the energy density of the light beam entering said device.

8. The tapered liquid light guide according to claim 7, wherein the coupling means includes an attachment mechanism.

9. The tapered liquid light guide according to claim 7, wherein the coupling means includes placing the laser catheter within the tapered liquid light guide.

10. The tapered liquid light guide according to claim 7, wherein the concentrating means comprises a taper in the physical structure of the tapered liquid light guide, wherein the taper substantially internally reflects light toward an exit aperture at the distal end.

11. The tapered liquid light guide according to claim 7, wherein the directing means includes a liquid medium.

12. The tapered liquid light guide according to claim 7, wherein the elongated tubular structure surrounds a substantial portion of the laser catheter.

13. The tapered liquid light guide according to claim 7, wherein the coupling means comprises attaching the proximal end of the tapered liquid light guide with the distal end of the laser catheter.

14. The tapered liquid light guide according to claim 7, wherein the coupling means comprises placing at least the distal end of the laser catheter within the elongated tubular structure.

15. A tapered liquid light guide configured to increase energy density of light emanating from a laser catheter, the tapered liquid light guide comprising:

a distal end with a distal aperture;

a proximal end with a proximal aperture such that the cross-section of the proximal aperture is greater than the cross-section of the distal aperture;

coupling means for mechanically and detachably coupling the proximal end to a distal end of the laser catheter; and a body including an inner lumen, wherein at least a portion of the inner lumen is tapered from a first cross-section adjacent to the proximal end to a second cross-section adjacent to the distal end, wherein the first cross-section is greater than the second cross-section, wherein the body is configured to support the laser catheter within the inner lumen, the inner lumen configured to allow a liquid medium to flow toward the distal end, and wherein at least a portion of the tapered portion of the inner lumen is constructed from a material configured to induce internal reflection of light within the liquid medium.

16. The tapered liquid light guide according to claim 7, further comprising a liquid medium infusion port at or near the proximal end.

17. The tapered liquid light guide according to claim 7, wherein the liquid medium comprises a biocompatible solution.

18. The tapered liquid light guide according to claim 7, wherein the liquid medium comprises a solution comprising a salt selected from the group consisting of $MgCl_2$, NaCl and CaCl.

19. The tapered liquid light guide according to claim 7, wherein the liquid medium comprises a salt solution.

20. The tapered liquid light guide according to claim 1, wherein the tapered portion of the inner lumen is constructed of a material having an index of refraction below 1.4 at a wavelength of 308 nm.

21. The tapered liquid light guide according to claim 10, wherein the taper is constructed of a material having an index of refraction below 1.4 at a wavelength of 308 nm.

* * * * *